US00PP21249P2

(12) United States Plant Patent
Stewart

(10) Patent No.: US PP21,249 P2
(45) Date of Patent: Aug. 31, 2010

(54) ***HARDENBERGIA VIOLACEA* PLANT NAMED 'RAMBOSPRAY'**

(50) Latin Name: *Hardenbergia violecea*
Varietal Denomination: Rambospray

(75) Inventor: Ian Angus Stewart, Somersby (AU)

(73) Assignee: Ramm Botanicals Holdings Pty., Ltd., Tuggerah, NSW (AU)

( * ) Notice: Subject to any disclaimer, the term of this patent is extended or adjusted under 35 U.S.C. 154(b) by 0 days.

(21) Appl. No.: 12/455,987

(22) Filed: Jun. 10, 2009

Related U.S. Application Data

(60) Provisional application No. 61/135,686, filed on Jul. 23, 2008.

(51) Int. Cl.
*A01H 5/00* (2006.01)

(52) U.S. Cl. ..... Plt./263.1

(58) Field of Classification Search ..... Plt./263.1, Plt./226
See application file for complete search history.

(56) References Cited

OTHER PUBLICATIONS

Australian Plant Breeder's Rights Application No. 2008/206 filed Jul. 15, 2008 http://pbr.ipaustralia.plantbreeders.gov.au/.

*Primary Examiner*—Annette H Para
(74) *Attorney, Agent, or Firm*—Audrey Charles

(57) ABSTRACT

A new and distinct cultivar of *Hardenbergia violacea* plant named 'Rambospray', characterized by its purple-colored flowers, upright and compact plant growth habit, freely branching, dense growth, lightly twining stem, early flowering season, erect inflorescence attitude, and a high level of flower production.

1 Drawing Sheet

Latin name of genus and species of plant claimed: *Hardenbergia violacea.*

Variety denomination: 'Rambospray'.

BACKGROUND OF THE INVENTION

The present invention relates to a new and distinct perennial variety of *Hardenbergia violacea*, which has been given the variety denomination of 'Rambospray'. Its market class is that of an ornamental plant. 'Rambospray' is intended for use in landscaping and as a decorative plant.

The new *Hardenbergia violacea* cultivar is a seedling selection discovered in a controlled planting of the species *Hardenbergia violacea*, not patented. The new cultivar was discovered and selected as a single plant within a population of plants of *Hardenbergia violacea* during June 2003 in a controlled environment at Tuggerah, New South Wales, Australia.

Asexual reproduction of the new cultivar by in vitro propagation of micro-plants since September 2006 at Tuggerah, New South Wales, Australia has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Rambospray' as a new and distinct cultivar of *Hardenbergia violacea* plant:

1. Purple-colored flowers;
2. Upright and compact plant growth habit;
3. Freely branching;
4. Dense growth;
5. Lightly twining stem;
6. Early flowering season;

7. Erect inflorescence attitude; and
8. A high level of flower production.

Plants of the new cultivar differ from plants of the *Hardenbergia violacea* parent species primarily in having a shorter plant height with a shorter, less twining stem and earlier time to first flower.

Of the many commercially available *Hardenbergia violacea* cultivars, the most similar in comparison to the new cultivar is 'Sweet Heart', not patented. However, in side by side comparisons, plants of the new cultivar differ from plants of 'Sweet Heart' in at least the following characteristics:

1. Plants of the new cultivar have an earlier time to first flower than plants of 'Sweet Heart'; and
2. Plants of the new cultivar have a darker purple flower color than plants of 'Sweet Heart'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Rambospray'.

DETAILED BOTANICAL DESCRIPTION

Figure 1:
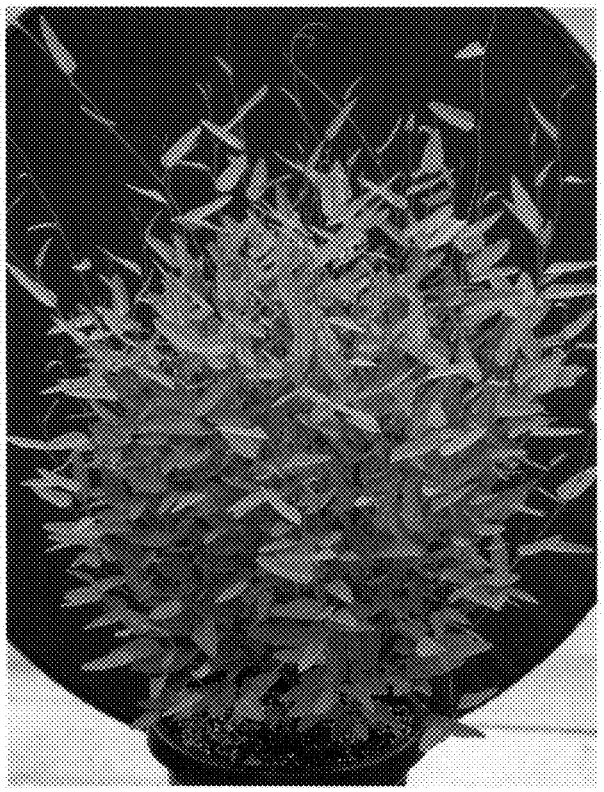
FIG. 1 illustrates a 'Rambospray' plant in a 40 cm pot grown for approximately 60 weeks.
Figure 2:
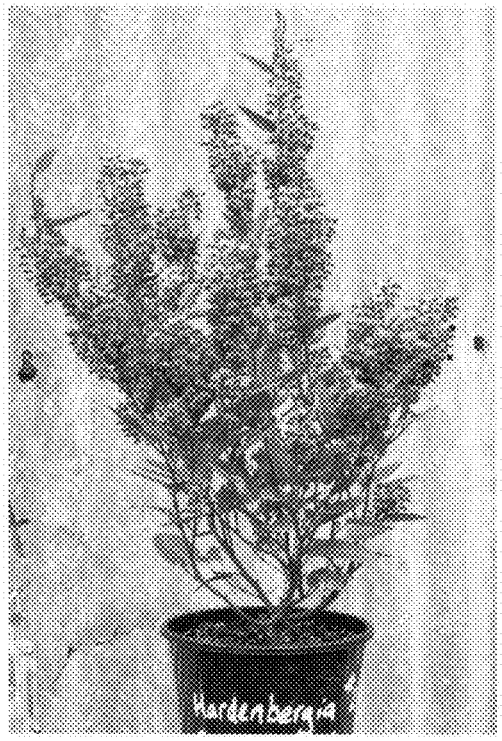
FIG. 2 illustrates a 'Rambospray' plant in a 20 cm pot grown for approximately 26 weeks.
Figure 3:
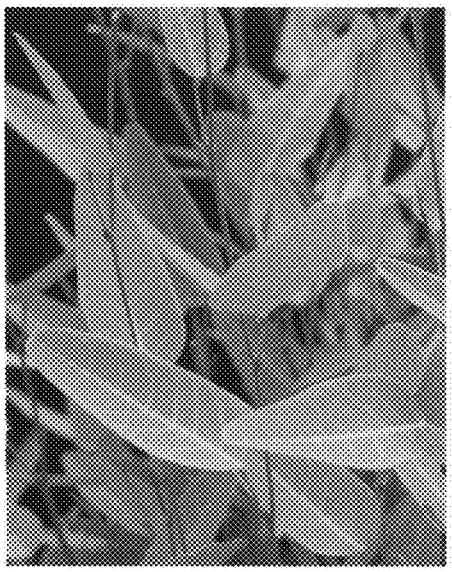
FIG. 3 illustrates a close-up view of the foliage of 'Rambospray'.
Figure 4:
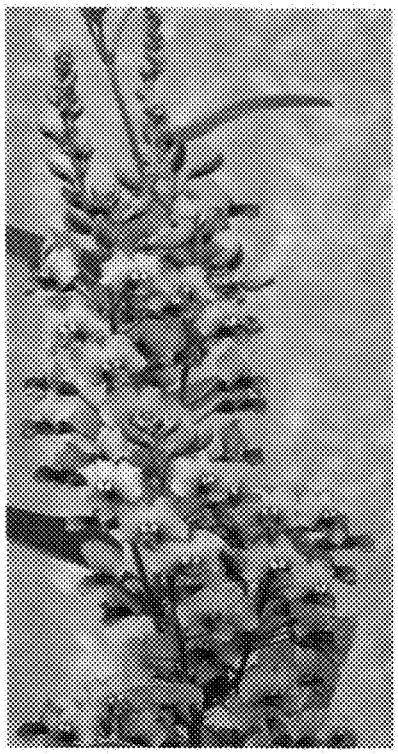
FIG. 4 illustrates a close-up view of an individual inflorescence of 'Rambospray'.

The following is a detailed botanical description of a new and distinct variety of a *Hardenbergia violacea* ornamental plant known as 'Rambospray'. Plant observations were made on plants grown in Tuggerah, New South Wales, Australia. Unless indicated otherwise, the descriptions disclosed herein are based upon observations made from June 2008 of mature 'Rambospray' plants grown in nursery pots in greenhouse and outdoor growing areas with day temperature ranging from 25° C. to 27° C., night temperatures ranging from 6° C. to 8° C., and light levels ranging from 6 to 8 klux. Plants were grown for about 60 weeks with one plant per 40 cm container. Those skilled in the art will appreciate that certain characteristics will vary with older or, conversely, younger plants. 'Rambospray' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on The Royal Horticultural Society Colour Chart, of The Royal Horticultural Society, London, 2007 edition.

Botanical classification: *Hardenbergia violacea* cultivar Rambospray.

Parentage:

*Parent.*—*Hardenbergia violacea* species, not patented.

Propagation:

*Type.*—Cuttings.

*Time to initiate roots, summer.*—About 10 to 14 days at a temperature of approximately 25° C.

*Time to initiate roots, winter.*—About 20 days at a temperature of approximately 15° C.

*Time to produce a rooted plant, summer.*—About 21 to 28 days at a temperature of approximately 25° C.

*Time to produce a rooted plant, winter.*—About 30 to 35 days at a temperature of approximately 15° C.

*Root description.*—Thick, freely branching and white in color.

*Rooting habit.*—Freely branching.

Plant description:

*Plant and growth habit.*—Compact, upright, bushy and outwardly spreading plant habit with lightly twining stems with purple-colored flowers on erect inflorescences borne from axillary positions on the stem. Moderately vigorous growth habit.

*Plant height.*—Average plant height including the inflorescence is about 110 cm (range 100 to 120 cm) in a garden plant grown in soil.

*Plant diameter.*—Average plant spread of a mature plant grown in a garden plant grown in soil in Tuggerah, New South Wales, Australia is 130 cm (observed winter 2008).

*Stem.*—Freely branching with short internode length (range 3.0 to 4.5 cm), diameter of new season growth 2.0 to 3.0 mm. Color of immature stem: 166A. Color of mature stem: 195A striped with 166B. Texture: Smooth, glabrous twining of stem is light (usually less than 20 cm) compared to wild types which may climb to a height of 2 m.

Foliage description:

*General description* .—Leaf attitude is horizontal/semi-erect. Arrangement: alternate, simple; petiolate.

*Leaves.*—Length: About 70 to 75 mm in a mature plant. Width: About 26 to 35 mm. Shape: Ovate. Apex: Obtuse in profile with inconspicuous mucronulate type point hooked away to underside . Base: Subcordate. Margin: Entire. Texture, upper and lower surfaces: Smooth, glabrous. Venation pattern: pinnate. Immature leaf: Color of the upper and lower surfaces: N199B. Mature leaf: Color of the upper surface: 147A. Color of the lower surface: 191A. Petiole: length 1.0 to 1.4 cm, color on a new leaf 176A, color on an older leaf 146C.

Flower description:

*General description.*—Flowers arranged singly on axillary racemes. Freely flowering, non-persistent. Inflorescence: attitude is erect, length of raceme about 10.0 to 12.5 cm, diameter of raceme: About 3.5 to 4.5 cm. Number of flowers per raceme is 26 to 34. Flower diameter: About 1.2 cm measured across the standard petal. Flower height: About 9.0 mm measured from the top of the standard petal to the base of the keel petal.

*Natural flowering season.*—'Rambospray' has an early flowering season under outdoor growing conditions commencing in early June and continuing to late September in Tuggerah, New South Wales, Australia.

*Bud just before opening.*—Length: About 5.0 mm. Width: About 3.0 mm. Texture: smooth. Color: N81A.

*Petals.*—Arrangement: typical pea type flower with standard, wing and keel petals. Standard petal: width: 12 mm, height 9.0 mm, shape rounded, margin entire. Wing petals: length: 5.0 mm, width 3.5 mm, shape obovate, margin entire. Keel petal: shape falcate, margin entire, length: 3.5 to 4.0 mm, width 2 mm. Main color of all petals upper side and lower side N82A. Markings on standard petal present and forming a symmetrical pattern from basal section of midrib (eye like pattern), marking lengths about 3.0 mm, marking widths about 1.3 mm, color of markings 150C.

*Calyx.*—Length: About 4.0 mm. Sepals united. Texture: smooth. Color: 146A with anthocyanin coloration of 187A.

*Peduncle* (*flowering stems*).—Strength: Strong, flexible. Attitude: Erect. Length: About 2.5 cm. Diameter at base: About 3.0 mm. Texture: smooth. Color: 176A.

*Pedicels* (*individual flower stems*).—Length: About 7.5 mm (range 5.5 to 8.5 mm). Diameter: About 0.5 mm. Strong and flexible. Color: 176A.

Seed and fruit production: Pod length: 3.0 to 5.0 cm. Pod Color: immature color of 147A maturing to 200A. Seed length: Approximately 5.0 mm. Seed color: 197A.

Disease and pest resistance: Resistance to pathogens and pests common to *Hardenbergia* has not been observed.

What is claimed is:

1. A new and distinct cultivar of *Hardenbergia violacea* plant named 'Rambospray', substantially as herein shown and described.

* * * * *